United States Patent [19]

Buske et al.

[11] Patent Number: 5,288,922
[45] Date of Patent: Feb. 22, 1994

[54] PROCESS OF PREPARING DIARYL ETHERS OVER A DEALUMINATED ZEOLITE CATALYST

[75] Inventors: Gary R. Buske; Juan M. Garces; William P. Dianis, all of Midland, Mich.

[73] Assignee: The Dow Chemical Company, Midland, Mich.

[21] Appl. No.: 915,161

[22] Filed: Jul. 16, 1992

[51] Int. Cl.$^5$ ............................................. C07C 41/09
[52] U.S. Cl. .................................. 568/635; 568/632; 568/633; 568/636
[58] Field of Search ................ 568/635, 636, 632, 633

[56] References Cited

U.S. PATENT DOCUMENTS

| | | | |
|---|---|---|---|
| 2,782,239 | 2/1957 | Mavity | 260/613 |
| 3,886,218 | 5/1975 | Biller et al. | 260/613 R |
| 3,987,105 | 10/1976 | Yardley | 260/600 R |
| 4,092,364 | 5/1978 | Smith | 260/612 R |
| 4,306,094 | 12/1981 | Shozda | 568/637 |
| 4,306,106 | 12/1981 | Kerr et al. | 585/640 |
| 4,360,699 | 11/1982 | Wright | 568/635 |
| 4,528,406 | 7/1985 | Arnold et al. | 568/659 |
| 4,536,485 | 8/1985 | Topp-Jorgensen | 502/62 |
| 4,596,680 | 6/1986 | Jost et al. | 560/424 |
| 4,891,448 | 1/1990 | Garces et al. | 568/628 |
| 4,898,982 | 2/1990 | Hussmann | 568/58 |
| 5,004,841 | 4/1991 | Lee et al. | 568/678 |

FOREIGN PATENT DOCUMENTS

| | | |
|---|---|---|
| 0317208 | 11/1988 | European Pat. Off. |
| 530736 | 7/1931 | Fed. Rep. of Germany |
| 59-196835 | 4/1983 | Japan |
| 6372640 | 9/1986 | Japan |
| 914546 | 10/1979 | U.S.S.R. |

OTHER PUBLICATIONS

Chantal P., et al. Reactions of Phenolic Compounds over HZSM-5, *Applied Catalysis*, 18 (1985), 133–145.

Chantal P. et al., Reactions of Phenolic Compounds on H-ZSM-5, *Aud. Surf. Sci Catal.* 19 (1984) 93–100.

Claes, F., et al. Quantitative Kinetics in Heterogeneous Catalysis. The Dehydration of Phenols Over Thoria. *Bull. Soc. Chim. Fr.*, (1962), 1042–1046.

Fravel, H. Jr., Evolution of a Process: The Manufacture of Diphenyl Oxide, *J. Chem. Ed.* vol. 57, No. 12, Dec. (1980), 873–4.

Karuppannasamy, S., Investigations of Phenol Decomposition on Thoria Catalysts *Proc. Natl. Symp Catal.* (1980) 443–50.

Karuppannasamy, S., Reactions of Phenols and Alcohols over Thoria, *Journal of Catalysis*, 63 (1980), 433–437.

Karuppannasamy, S., Reactions of Phenols and Alcohols over Thoria: Mechanism of Ether Formation, *Journal of Catalysis*, 66 (1980), 281–289.

Weingarten, H., Ullmann Condensation, Apr. (1964), 977–979.

Weingarten, H., Mechanism of the Ullmann Condensation, Dec. (1964), vol. 29, 3624–3626.

*Primary Examiner*—James H. Reamer
*Assistant Examiner*—Margaret J. Page
*Attorney, Agent, or Firm*—Marie F. Zuckerman

[57] ABSTRACT

A process of preparing diaryl ethers, such as diphenyl oxide, involving dehydrating a hydroxy-substituted aromatic compound, such as phenol, over a zeolite catalyst. The preferred zeolites are dealuminated acid mordenite and dealuminated zeolite Y.

27 Claims, No Drawings

PROCESS OF PREPARING DIARYL ETHERS OVER A DEALUMINATED ZEOLITE CATALYST

BACKGROUND OF THE INVENTION

This invention relates to a process of preparing diaryl ethers.

Diaryl ethers, such as diphenyl oxide, are useful as high temperature solvents and as components in heat transfer fluids and perfumes. In addition, diaryl ethers are intermediates in processes of preparing flame retardants and surfactants.

U.S. Pat. No. 4,092,364 discloses the production of diphenyl oxide by the caustic hydrolysis of chlorobenzene. Because the process operates at about 400° C. and about 5000 psig pressure, an expensive alloy reactor is required. As a further disadvantage, several organic byproducts are formed which are not readily marketed. Even more disadvantageously, stoichiometric quantities of sodium chloride are produced as a byproduct which must be disposed.

U.S. Pat. No. 4,360,699 discloses a process of preparing diphenyl oxide comprising contacting phenol with aluminum. This reaction presumably proceeds by forming aluminum triphenate which then pyrolyzes to diphenyl ether and alumina. Disadvantageously, the reaction is stoichiometric in aluminum, requires high temperatures, and forms a solid aluminum oxide as a byproduct.

The most general method for making diaryl ethers is the Ullman condensation which allows for the preparation of a variety of symmetrical and unsymmetrical diaryl ethers. In this method, illustrated by the disclosure of H. Weingarten in the *Journal of Organic Chemistry*, 29, 1964, 977 and 3624, a metal phenate, such as potassium phenate, is reacted with a halobenzene, such as chlorobenzene, over a copper catalyst to yield the desired diaryl ether. As a disadvantage, this method produces stoichiometric quantities of metal halide as a byproduct which must be disposed.

It is also known to prepare diaryl ethers by the pyrolysis of diaryl carbonates, as disclosed in U.S. Pat. No. 4,596,680. Diaryl carbonates are typically manufactured by the reaction of phenols with phosgene. The latter reactant is undesirable for safety reasons. Moreover, when two equivalents of phenol react with one equivalent of phosgene, two equivalents of hydrogen chloride are produced as a byproduct. The hydrogen chloride must be neutralized with base which yields a waste salt stream which must be disposed.

It would be more desirable to prepare diaryl ethers simply by the dehydration of phenols. The dehydration was first reported by P. Sabatier and A. Mailhe in *Compt. Rend.*, 151, 1910, 492–494, who passed phenol over a thoria catalyst at 410° C. and atmospheric pressure to obtain diphenyl oxide and dibenzofuran as a byproduct. More recently, F. Claes and J. C. Jungers (Bull. Soc. Chim. Fr., 1962, 1042) evaluated the kinetics of phenol dehydration to diphenyl ether over thoria supported on pumice. They reported equilibrium data at temperatures from 400° C. to 438° C. Based on their data, it can be concluded that the reaction to form diphenyl ether is endothermic at temperatures below 460° C. and exothermic at temperatures higher than that. At 400° C. the equilibrium phenol conversion is only 37.0 weight percent. At 438° C. the equilibrium phenol conversion is 57.1 weight percent.

In addition to the above, British Patent 911,246 discloses the dehydration of phenols to diphenyl oxides over thoria supported on alpha-alumina, and U.S. Pat. No. 4,898,982 discloses the dehydration of phenols to diphenyl oxides over thoria deposited on a neutral support, such as pure silica, pure zirconia, carbon or asbestos. Although the processes employing thoria provide good yields of diaryl ethers, the processes suffer from at least one serious disadvantage. Thoria is radioactive; thus, extra precautions are required to handle the catalyst, disposal options are limited, and government licensing is required.

There are very few examples of catalysts other than thoria which successfully dehydrate phenols to diaryl ethers. Japanese Patent Kokai No. 59-196835 discloses a process wherein a phenol is brought into contact with titanium oxide or zirconium oxide in the vapor phase to yield diaryl ethers. In the best example, a 37 percent conversion of phenol is achieved with 82 percent selectivity to diphenyl ether. Disadvantageously, the yield of diphenyl ether is only 30 percent at best.

Japanese Patent 63-72640 discloses a method of preparing diphenyl ethers in which phenol and/or a substituted phenol is brought into contact in the liquid phase with a catalyst containing a crystalline metal silicate whose molar ratio of silicon oxide to trivalent metal oxide, $SiO_2/M_2O_3$, is at least 12, and preferably, in the range from 40 to 3,000. "M" may be aluminum. The metal silicates disclosed by this patent include crystalline metal silicates having a pentasil structure or zeolites with a ZSM-5 structure. It is taught that after 20 hours at 300° C. the phenol conversion is 43 mole percent and the selectivity to the ether is 90 mole percent. Disadvantageously, this process requires pre-pressurization to high pressures.

U.S. Pat. No. 4,536,485 broadly disclose the preparation of alkyl and aryl ethers from aliphatic and aromatic alcohols. Synthetic zeolites, specifically ZSM-5 and zeolite Y, are taught to be useful catalysts for the process. A method of treating the catalyst is taught to improve catalytic lifetime.

In view of the above, it is clear that a need exists to find a method of producing diaryl ethers which is selective and efficient and which minimizes waste formation and does not use phosgene or radioactive materials.

SUMMARY OF THE INVENTION

In one aspect, this invention is a process of preparing a diaryl ether comprising contacting a hydroxy-substituted aromatic compound with a catalytic amount of a zeolite selected from the group consisting of dealuminated acid mordenite, dealuminated zeolite L and zeolite $\beta$. The dealuminated acid mordenite is characterized as having a silica to alumina molar ratio of at least about 40. The zeolites $\beta$ and L are characterized as having a silica to alumina molar ratio of at least about 20. The contacting of the hydroxy-substituted aromatic compound with the mordenite zeolite is carried out under reaction conditions such that the diaryl ether is formed.

In another aspect, this invention is a process of preparing a diaryl ether comprising contacting a hydroxy-substituted aromatic compound with a catalytic amount of a dealuminated zeolite Y having a silica to alumina molar ratio of at least about 20. The contacting of the hydroxy-substituted aromatic compound with the dealuminated zeolite Y is conducted at a temperature in the range from about 200° C. to about 300° C. and under reaction conditions such that the diaryl ether is formed in high selectivity. The dealuminated zeolite Y catalyst is capable of achieving a selectivity to diaryl ether, measured as the weight percentage of diaryl ether in the observed products excluding hydroxy-substituted aromatic compound and optional diluent or solvent, of greater than about 70 weight percent at a temperature in the range from about 200° C. to about 300° C.

Advantageously, the above-identified processes of this invention are capable of dehydrating a hydroxy-substituted aromatic compound to a diaryl ether in high selectivity. In preferred embodiments, the process simultaneously achieves a high conversion of hydroxy-substituted aromatic compound as well as high selectivity to diaryl ether. Under these conditions a high yield of diaryl ether is obtained. As a further advantage, the dehydration processes of this invention can be conducted at low temperature and autogenous pressure while still achieving a rapid reaction rate. Even more advantageously, the processes of this invention do not produce a waste salt stream which would present a disposal problem. Most advantageously, the processes of this invention do not require phosgene or radioactive materials.

The diaryl ethers which are produced by the dehydration processes of this invention are useful as high temperature solvents, as intermediates in preparing flame retardants and surfactants, and as components in heat transfer fluids and fragrance formulations.

DETAILED DESCRIPTION OF THE INVENTION

Hydroxy-substituted aromatic compounds which are suitable for use in either dehydration process of this invention include phenols and α- and β-hydroxy-substituted fused aromatic ring systems. Apart from the hydroxy substituent, the compounds may be unsubstituted, as in phenol or naphthol. Optionally, however, the compounds may be further substituted with at least one alkyl group containing from 1 to about 10 carbon atoms, preferably, from 1 to 3 carbon atoms, or substituted with at least one alternative substituent which is inert to the dehydration coupling reaction. Suitable inert substituents include cyano, amino, nitro, carboxylic acid, ester, alkyloxy and phenoxy moieties. It is also possible for the hydroxy-substituted aromatic compound to be substituted with both an alkyl substituent and one of the alternative inert substituents. Each of the aforementioned alkyl substituents and/or alternative inert substituents is attached preferably to an aromatic ring carbon atom which is located in a meta or para position relative to the hydroxy moiety. Optionally, the alkyl substituent may contain from 3 to 4 carbon atoms, and in combination with a phenol or fused aromatic ring system may form a saturated ring fused to the aromatic ring.

Non-limiting examples of suitable phenols include unsubstituted phenol, m-cresol, p-cresol, 3,4-xylenol, 3,5-xylenol, and 3,4,5-trimethylphenol. Other suitable phenols include compounds corresponding to the above-mentioned examples except that one or more of the methyl substituents are replaced by an ethyl, propyl or butyl substituent. Non-limiting examples of α- and β-hydroxy-substituted fused aromatic ring systems include α- and β-naphthol and 5-tetralinol. One skilled in the art may find other phenols and α- and β-hydroxy-substituted fused aromatic ring systems which are also suitable for the purposes of this invention. Preferably, the hydroxy-substituted aromatic compound is unsubstituted phenol or a substituted phenol wherein the substituent is methyl or ethyl. More preferably, the hydroxy-substituted aromatic compound is unsubstituted phenol or cresol. Most preferably, the hydroxy-substituted aromatic compound is unsubstituted phenol.

Ideally, the hydroxy-substituted aromatic compound is employed neat, but optionally, the processes of this invention can be conducted with a gaseous diluent or liquid solvent as a component of the feedstream, as noted hereinbelow.

It has now been discovered that when the above-identified hydroxy-substituted aromatic compound is brought into contact with a catalytic amount of a crystalline aluminosilicate zeolite, identified hereinafter, that the dehydration of the aromatic compound occurs to yield a diaryl ether. Generally, the zeolite is one which contains a twelve-membered ring system. It is known that zeolites are constructed from primary building units comprising $AlO_4$ and $SiO_4$ tetrahedra. A twelve-ring zeolite is one which contains a ring system formed from twelve of such tetrahedra. Twelve-ring zeolites which are suitable for the process of this invention include mordenite and zeolites Y, β, L, and ZSM-12. Preferred zeolites for the dehydration process of this invention include dealuminated acid mordenite, dealuminated zeolite Y and zeolite β. More preferred is dealuminated acid mordenite.

Significantly, it has now been further discovered that the selectivity to diaryl ether in the dehydration processes of this invention varies with the silica to alumina molar ratio of the zeolite catalyst. Accordingly, the zeolites employed in the process of this invention beneficially possess a silica to alumina molar ratio of at least about 20. Zeolite β can be directly synthesized with a silica to alumina molar ratio of 20 or higher. On the other hand, mordenite and zeolites Y and L are typically synthesized having silica to alumina molar ratios lower than 20. Accordingly, these zeolites can be dealuminated to remove a portion of the alumina from the framework and pores so as to prepare a zeolite having a silica to alumina molar ratio of 20 or greater. Dealumination techniques are well-known to those skilled in the art.

A preferred dealuminated acid mordenite has been thoroughly described in U.S. Pat. Nos. 4,891,448 and 5,004,841, relevant portions of which are incorporated herein by reference. For the convenience of the reader, significant features of the preferred mordenite and its preparation are summarized hereinafter.

The starting mordenite may be any sodium mordenite containing a crystalline phase of Cmcm symmetry and a second crystalline phase of Cmmm symmetry, the crystalline phases being determined by X-ray diffraction (XRD) analysis. The proper balance of Cmcm and Cmmm phases is determined by choosing a mordenite having a Symmetry Index between about 0.5 and about 1.3, and preferably, between about 0.6 and about 1.3. The Symmetry Index is obtained from the XRD spectrum and is defined as the sum of the peak heights of the [111] (13.45, 2θ) and [241] (23.17, 2θ) reflections divided by the peak height of the [350] (26.25, 2θ) reflection. The starting sodium mordenite is converted to the acid form by ion-exchange with a weak acid solution, this technique being known to those skilled in the art. If the starting mordenite is already in the acid form, then the acid ion-exchange step is not necessary. Thereafter, the acid mordenite is calcined, preferably at a temperature ranging from about 300° C. to about 800° C. Finally, the calcined mordenite is acid-extracted with an aqueous solution of a strong acid, such as nitric, sulfuric or hydrochloric acid, at a normality preferably in the range from about 2N to about 15N for a time sufficient to remove alumina so as to yield a dealuminated acidic mordenite having a silica to alumina molar ratio of at least about 40. The calcination and acid extraction steps may be repeated one or more times, as necessary.

The above-identified preparation yields the preferred dealuminated acidic mordenite zeolite which can be characterized by certain critical features. As noted hereinbefore, the silica to alumina molar ratio is increased over that of the starting mordenite. For the purposes of this invention, the dealuminated mordenite possesses a silica to alumina molar ratio of at least about 40. Preferably, the dealuminated mordenite possesses a silica to alumina molar ratio of at least about 50, more preferably, in the range from about 50 to about 500, even more preferably, from about 100 to about 300, and most preferably, from about 100 to about 250. In addition, the preferred dealuminated mordenite contains a Symmetry Index which is at least about 1.0, and preferably, in the range from about 1.0 to about 2.0, more preferably, in the range from about 1.5 to about 2.0. As a third property, the preferred dealuminated mordenite possesses a total pore volume in the range from about 0.18 cc/g to about 0.45 cc/g and a ratio of combined meso- and macropore volume to total pore volume in the range from about 0.25 to about 0.75.

Typically, the dealuminated Y zeolite possesses a silica to alumina molar ratio of at least about 20. Preferably, the Y-zeolite possesses a silica to alumina molar ratio in the range from about 20 to about 600, more preferably from about 25 to about 100, most preferably, from about 35 to about 70.

When employed in the processes of this invention, the catalysts can become deactivated over a period of time due to the presence of coke. Typically, coking is more of a problem when the process is run in the vapor phase rather than in the liquid phase where the liquid can carry off some of the coked products. Regeneration may be simply effected by first purging the spent catalyst of residual hydroxy-substituted aromatic compound and then burning the purged catalyst in oxygen or air. Nitrogen alone does not appear to purge the system thoroughly of residual hydroxy-substituted aromatic compound; thus, the preferred purge is conducted with steam. Optionally, the burn-off step may be conducted in the presence of a inert, gaseous diluent, such as nitrogen. The temperature at burn-off typically ranges from about 300° C. to about 700° C., more preferably, from about 350° C. to about 650° C., most preferably, from about 500° C. to about 600° C.

The dehydration processes of this invention can be conducted in the liquid or vapor phase. If carried out in the vapor phase, the hydroxy-substituted aromatic compound is preheated to a temperature high enough to yield an operable vapor pressure, but below the decomposition temperature of the compound. The heated vapor is then contacted with the catalyst under reaction conditions. The temperature at which a sufficient vapor pressure is obtained will vary from compound to compound, but typically, will be in the range from about 180° C. to about 600° C. Optionally, the vapor phase process may contain a gaseous diluent which is substantially inert under the process conditions. The gaseous diluent serves as a carrier gas to sweep the hydroxy-substituted aromatic compound through the catalyst bed. Suitable gaseous diluents include nitrogen, hydrogen, helium, and argon. Typically, the concentration of hydroxy-substituted aromatic compound in the gaseous diluent is at least about 10 volume percent. Preferably, the concentration of hydroxy-substituted aromatic compund in gaseous diluent is in the range from about 50 to about 100 volume percent, more preferably, from about 90 to about 100 volume percent.

Preferably, the dehydration processes of this invention are conducted in the liquid phase. Advantageously, conversion tends to be higher and catalyst lifetime tends to be longer when the process is conducted in this manner. Typically, the hydroxy-substituted aromatic compound is preheated to a molten liquid or dissolved in a suitable solvent which is then contacted with the catalyst under reaction conditions. Suitable solvents should be substantially inert with respect to the dehydration process. Non-limiting examples of suitable solvents include aromatic hydrocarbons which are liquid at the reaction conditions of the process. Preferably, the solvent is an aromatic hydrocarbon containing from about 6 to about 12 carbon atoms, such as benzene, toluene, xylene, and mesitylene. The solvent may also be one which forms an azeotrope with the water formed during dehydration of the hydroxy-substituted aromatic compound. In this manner, the equilibrium of the dehydration process can be pushed towards products. As an example, a suitable solvent which forms an azeotrope with water is benzene.

The concentration of hydroxy-substituted aromatic compound in the optional liquid solvent is any which produces the diaryl ether product in high selectivity. Typically, the concentration of hydroxy-substituted aromatic compound in liquid solvent is at least about 10 weight percent. Preferably, the concentration of hydroxy-substituted aromatic compound in liquid solvent is in the range from about 50 to about 100 weight percent, more preferably, from about 90 to about 100 weight percent. Most preferably, no solvent is used.

Since water is produced as a byproduct in the processes of this invention, it is preferable to keep water out of the feedstream. In this way, the equilibrium of the process is driven towards the product side of the equation. On the other hand, water may be a component of the feedstream without upsetting the selectivity of the process.

Any reactor is suitable for the dehydration processes of this invention provided that the desired diaryl ether product is formed in high selectivity. Suitable reactors include stirred tank and high pressure batch reactors, fixed-bed continuous flow reactors, fluidized bed continuous flow reactors, and conventional batch reactors equipped with a distillation column for azeotropic distillation of products, as well as less conventional reactive distillation columns.

Any operable temperature is suitable for the dehydration process of this invention employing the acid mordenite catalyst provided that the diaryl ether product is achieved in high selectivity. Typically, the process temperature ranges from about 200° C. to about 550° C. Preferably, the temperature ranges from about 200° C. to about 450° C., more preferably from about 200° C. to about 350° C., most preferably from about 250° C. to about 350° C. Above the preferred upper limit of about 450° C. selectivity to diaryl ether may decrease. Below about 200° C. conversion of the hydroxy-substituted aromatic compound may be too low.

With respect to the zeolite Y catalyst the process temperature typically ranges from about 200° C. to about 300° C., preferably from about 225° C. to about 275° C. Above the upper limit of about 300° C. selectivity to diaryl ether decreases. Below about 200° C. conversion of the hydroxy-substituted aromatic compound may be too low.

The dehydration processes of this invention may be maintained at any operable pressure provided that diaryl ether is achieved in high selectivity. Typically, when the process is carried out in the vapor phase, the pressure ranges from sub-atmospheric to about 200 psig, preferably, from about atmospheric to about 50 psig. Alternatively, when the process is carried out in the liquid phase, the pressure typically ranges from sub-atmospheric to about 1500 psig, but preferably, is autogenous.

When the process is conducted in a continuous flow reactor, any operable weight hourly space velocity is suitable provided that diaryl ether is achieved in high selectivity. Typically, the weight hourly space velocity (WHSV), given in units of g hydroxy-substituted aromatic compound per g catalyst per hour or simply $hr^{-1}$, ranges from about 0.01 $hr^{-1}$ to about 10 $hr^{-1}$. Preferably, the WHSV ranges from about 0.05 $hr^{-1}$ to about 5 $hr^{-1}$, more preferably, from about 0.1 $hr^{-1}$ to about 2 $hr^{-1}$.

When the hydroxy-substituted aromatic compound is contacted with the dealuminated zeolite catalyst described hereinbefore, the hydroxy-substituted aromatic compound is dehydrated to yield a diaryl ether, and water is produced as a byproduct. For example, phenol is condensed to diphenyl oxide. Likewise, substituted phenols, such as m-cresol, are condensed to substituted diphenyl ethers, such as 3,3'-dimethyldiphenyl ether. In the case of naphthol, which is a fused aromatic ring system, dinaphthyl oxide is formed. Typical organic byproducts of the phenol dehydration include benzene, lights boiling between benzene and phenol, middles boiling between benzene and biphenyl, biphenyl, o-phenylphenol, dibenzofuran, and other unidentified higher boiling components. Separation of the product stream into essentially pure product fractions can be accomplished by standard techniques known to those skilled in the art, for example, distillation, extraction followed by phase separation, recrystallization, and crystal refining. Unreacted hydroxy-substituted aromatic compound can be recovered and recycled to the reactor, if desired.

For the purposes of this invention, the term "conversion" refers to the weight percentage of hydroxy-substituted aromatic compound which reacts to form products. Generally, conversion varies depending upon the process conditions, such as, temperature and space velocity and whether the process is conducted in the vapor or liquid phase. It has been observed, for example, that the conversion tends to decrease with increasing space velocity. Typically, the conversion achieved in the practice of this invention is at least about 3 weight percent, preferably, at least about 10 weight percent, more preferably, at least about 20 weight percent. More specifically, when the process is conducted in the liquid phase, the conversion is preferably at least about 30 weight percent, more preferably at least about 40 weight percent, most preferably, at least about 50 weight percent.

For the purposes of this invention, the term "selectivity" refers to the mole percentage of reacted hydroxy-substituted aromatic compound which is converted to a specific product, preferably, diaryl ether. Selectivities will also vary depending upon process conditions. For example, it has been observed that the selectivity to diaryl ether increases with decreasing reaction temperature, but remains fairly constant with respect to space velocities in the range from about 0.15 $hr^{-1}$ to about 0.50 $hr^{-1}$. When phenol is employed as the feedstream, the selectivity to diphenyl oxide is typically at least about 20 mole percent. Preferably, the selectivity to diphenyl oxide is at least about 40 mole percent, more preferably, at least about 50 mole percent, even more preferably, at least about 60 mole percent, and most preferably, at least about 80 mole percent. In general, the selectivity to diaryl ethers is at least about 20 mole percent, preferably at least about 40 mole percent, more preferably at least about 60 mole percent, and most preferably, at least about 80 mole percent.

Another measure of the selectivity to diaryl ether is given by the weight percentage of diaryl ether found in the observed products, excluding hydroxy-substituted aromatic compound and any optional diluent or solvent. This measurement is especially helpful at low conversions. Typically, in the dehydration processes of this invention the percentage of diaryl ether found in the observed products is at least about 20 weight percent. Preferably, the percentage of diaryl ether found in the observed products is greater than about 50 weight percent, more preferably, greater than about 70 weight percent, even more preferably at least about 80 weight percent, and most preferably, at least about 90 weight percent.

ILLUSTRATIVE EMBODIMENTS

The following examples are illustrative of the process of this invention, but should not be construed to be limiting thereof. All percentages are given in units of weight percent unless otherwise noted.

General Method for Vapor Phase Process

The equipment and general method described hereinbelow are employed in the Examples and Comparative Experiment conducted in the vapor phase. Approximately 10-15 grams of catalyst are loaded into a ½ inch o.d. stainless steel reactor tube to form a catalyst bed approximately 0.95 cm in diameter and 30 cm in length. The reactor tube is filled with quartz chips below the catalyst bed, such that the catalyst bed is supported in the furnace zone. The tube is also filled with quartz chips above the catalyst bed forming a second zone in the furnace. The purpose of the second zone is to preheat and vaporize the phenol feed to the desired reaction temperature. The preheat zone is approximately 0.95 cm in diameter by 27 cm in length. The reactor tube is placed in a vertical electric tube furnace and heated to the desired temperature. Molten phenol is pumped into the top of the reactor at the desired weight hourly space velocity. Samples are collected for 20-30 minutes and analyzed on a Hewlett-Packard Model 5890 gas chromatograph equipped with a flame ionization detector, a Model 7673 auto injector/sampler, and a Model 3396A integrator. Naphthalene is used as an internal standard. A 95% methyl (5% phenyl)silicone capillary column (0.25 mm by 30 m) with a film thickness of 1$\mu$ is employed. The oven is programmed at 80° C. for 2 min followed by heating at 16° C./min to 300° C. and then holding at 300° C. for 15 min. Phenol conversions are calculated by subtracting the GLC weight percent phenol from 100 weight percent. Selectivity is calculated as the mole percentage yield of diphenyl ether based on phenol converted, and is specifically given as:

$(100)[\%DPO/170.2]/[(100-\% \text{ phenol})/94.1]$

EXAMPLES 1-5

The fixed-bed, continuous flow, vapor phase process described hereinabove is employed. Examples 1-5 use a feed of phenol and a dealuminated acid mordenite zeolite catalyst having the following $SiO_2/Al_2O_3$ molar ratio: Example 1, 44; Example 2, 73; Example 3, 113; Example 4, 196; and Example 5, 220. The dealuminated mordenite zeolite catalysts are prepared according to the procedure described in U.S. Pat. No. 4,891,448. Catalysts are screened in the dehydration of phenol at temperatures ranging from 200° C. to 550° C. in 50° C. increments. Pressure in the reactor is atmospheric. Samples are taken within first hour of reaction time. The process conditions and results are set forth in Table I.

TABLE I

| Ex. | Catalyst | Temp. °C. | WHSV hr$^{-1}$ | % PhOH Conv.① | % DPO Sel.② | DPO as % of Observed Products③ |
|---|---|---|---|---|---|---|
| 1 | Mordenite $SiO_2Al_2O_3 = 44$ | 200 | 1 | 5.1 | 3.3 | 37.1 |
| | | 250 | 1 | 5.1 | 11.2 | 64.1 |
| | | 300 | 1 | 5.0 | 15.3 | 74.8 |
| | | 350 | 1 | 5.6 | 23.0 | 65.6 |
| | | 400 | 1 | 6.1 | 14.5 | 45.9 |
| | | 450 | 1 | 4.4 | 1.3 | 9.1 |
| | | 500 | 1 | 4.2 | 1.5 | 16.9 |
| | | 550 | 1 | 4.4 | 2.3 | 19.7 |
| 2 | Mordenite $SiO_2Al_2O_3 = 73$ | 200 | 1 | 2.5 | 3.9 | 18.5 |
| | | 250 | 1 | 4.2 | 1.0 | 20.2 |
| | | 300 | 1 | 4.7 | 1.4 | 27.6 |
| | | 350 | 1 | 4.9 | 1.5 | 21.9 |
| | | 400 | 1 | 3.9 | 0.4 | 11.5 |
| | | 450 | 1 | 4.4 | 0.7 | 10.8 |
| | | 500 | 1 | 4.5 | 2.0 | 20.8 |
| | | 550 | 1 | 5.8 | 4.0 | 20.4 |
| 3 | Mordenite $SiO_2/Al_2O_3 = 113$ | 200 | 1 | 0.8 | 52.4 | 77.5 |
| | | 250 | 1 | 2.1 | 81.5 | 92.8 |
| | | 300 | 1 | 9.2 | 86.4 | 95.4 |
| | | 350 | 1 | 8.8 | 80.1 | 89.1 |
| | | 400 | 1 | 6.9 | 66.6 | 74.9 |
| | | 450 | 1 | 5.2 | 51.0 | 58.5 |
| | | 500 | 1 | 3.5 | 52.9 | 61.3 |
| | | 550 | 1 | 3.3 | 51.0 | 57.4 |
| | | 300 | 0.08 | 43.0 | 53.7 | 80.5 |
| | | 300 | 0.19 | 37.2 | 70.3 | 91.1 |
| | | 300 | 0.27 | 32.9 | 84.9 | 93.6 |
| | | 300 | 0.46 | 23.4 | 77.8 | 92.6 |
| | | 325 | 0.21 | 35.4 | 60.5 | 83.9 |
| | | 325 | 0.31 | 27.8 | 71.1 | 86.4 |
| | | 350 | 0.20 | 31.1 | 56.2 | 76.1 |
| | | 350 | 0.24 | 34.8 | 52.3 | 76.5 |
| 4 | Mordenite $SiO_2Al_2O_3 = 196$ | 200 | 1 | 2.3 | 10.8 | 36.2 |
| | | 250 | 1 | 2.9 | 40.4 | 83.6 |
| | | 300 | 1 | 5.6 | 68.6 | 92.3 |
| | | 350 | 1 | 7.2 | 72.6 | 88.8 |
| | | 400 | 1 | 3.6 | 45.5 | 74.1 |
| | | 450 | 1 | 3.0 | 33.8 | 63.8 |
| | | 500 | 1 | 4.0 | 30.0 | 50.2 |
| | | 550 | 1 | 3.5 | 31.7 | 55.2 |
| 5 | Mordenite $SiO_2/Al_2O_3 = 220$ | 200 | 1 | 0.2 | 110.6 | 58.3 |
| | | 250 | 1 | 2.8 | 83.6 | 90.8 |
| | | 300 | 1 | 5.5 | 87.6 | 94.7 |
| | | 350 | 1 | 5.9 | 77.6 | 88.2 |
| | | 400 | 1 | 2.8 | 54.7 | 74.3 |
| | | 450 | 1 | 3.6 | 50.7 | 62.1 |
| | | 500 | 1 | 4.8 | 41.3 | 52.5 |
| | | 550 | 1 | 3.4 | 36.1 | 41.6 |
| 6 | Zeolite Y $SiO_2/Al_2O_3 = 25$ | 200 | 1 | 2.9 | 16.8 | 72.0 |
| | | 250 | 1 | 7.0 | 67.6 | 88.9 |
| | | 300 | 1 | 9.2 | 31.2 | 53.7 |
| | | 350 | 1 | 12.5 | 23.8 | 37.3 |
| | | 400 | 1 | 7.5 | 32.5 | 36.9 |
| | | 450 | 1 | 9.7 | 38.9 | 47.5 |
| | | 500 | 1 | 8.1 | 17.2 | 21.5 |
| | | 550 | 1 | 10.7 | 6.7 | 8.6 |
| 7 | Zeolite Y $SiO_2/Al_2O_3 = 50$ | 200 | 1 | 2.9 | 7.6 | 57.2 |

TABLE I-continued

| Ex. | Catalyst | Temp. °C. | WHSV hr⁻¹ | % PhOH Conv.[1] | % DPO Sel.[2] | DPO as % of Observed Products[3] |
|---|---|---|---|---|---|---|
| | | 250 | 1 | 3.6 | 68.9 | 93.8 |
| | | 300 | 1 | 6.5 | 54.6 | 74.1 |
| | | 350 | 1 | 7.0 | 40.1 | 56.2 |
| | | 400 | 1 | 9.8 | 42.7 | 49.3 |
| | | 450 | 1 | 5.2 | 51.9 | 59.6 |
| | | 500 | 1 | 7.4 | 31.4 | 39.0 |
| | | 550 | 1 | 8.4 | 9.4 | 10.9 |
| CE 1 | Y zeolite $SiO_2/Al_2O_3 = 6.2$ | 200 | 1 | 2.4 | 2.0 | 26.2 |
| | | 250 | 1 | 1.6 | 6.5 | 30.0 |
| | | 300 | 1 | 2.5 | 20.1 | 46.2 |
| | | 350 | 1 | 3.8 | 27.6 | 54.4 |
| | | 400 | 1 | 3.9 | 34.7 | 56.8 |
| | | 450 | 1 | 5.3 | 44.5 | 70.2 |
| | | 500 | 1 | 8.8 | 48.9 | 64.7 |
| | | 550 | 1 | 17.9 | 49.5 | 57.6 |

[1] Phenol (PhOH) conversion is calculated as 100 percent minus the GLC weight percent phenol.
[2] Selectivity to diphenyl oxide (DPO) is calculated as (100)[wt. % DPO/170.2]/[(100- wt. % phenol)/94.1(2)], based on GLC analysis.
[3] Calculated as 100(wt. % DPO)/(wt. % observed products excluding phenol and solvent), based on GLC analysis.

It is seen that a dealuminated mordenite zeolite catalyzes the vapor phase dehydration of phenol to diphenyl ether. For mordenite catalysts having a silica to alumina molar ratio greater than 100, the weight percentage of diphenyl ether in the observed products is greater than 90 percent at a temperature of only 300° C. Moreover, phenol conversion is seen to increase significantly at lower space velocities without loss in selectivity to diphenyl ether.

EXAMPLES 6 AND 7

Phenol is dehydrated in a vapor phase process similar to that employed in Examples 1-5 hereinabove, with the exception that the catalyst bed is filled with dealuminated Y zeolite (Conteka) having a $SiO_2/Al_2O_3$ molar ratio as follows: Example 6, 25; Example 7, 50. The reaction conditions and results are set forth in Table I. It is observed that dealuminated zeolite Y catalyzes the vapor phase dehydration of phenol to diphenyl ether. Moreover, the weight percentage of diphenyl ether in the observed products ranges from about 54 percent to about 94 percent at low process temperatures between 200° C. and 300° C.

COMPARATIVE EXPERIMENT 1

Phenol is dehydrated according to the vapor phase process employed in Examples 6 and 7 hereinabove, with the exception that the catalyst bed is filled with zeolite Y having a $SiO_2/Al_2O_3$ molar ratio of 6.2. The process conditions and results are set forth in Table I. It is seen that the best selectivity to diphenyl ether (DPO) is obtained at 450° C. where the percentage DPO in the observed products is 70.2 percent. When Examples 6 and 7 are compared with Comparative Experiment 1, it is observed that the dealuminated Y zeolites of the Examples, having a $SiO_2/Al_2O_3$ molar ratio of 25 or greater, achieve a higher selectivity to diphenyl ether at a lower reaction temperature than the dealuminated Y zeolite of the Comparative Experiment, having a $SiO_2/Al_2O_3$ molar ratio of 6.2. Specifically, the percentage DPO in the observed products of Examples 6 and 7 varies from about 54 to 94 percent at a reaction temperature of only 200° C. to 300° C.

EXAMPLE 8

Liquid Phase Process

Dealuminated mordenite catalyst (10 g) having a silica to alumina molar ratio of 113 is placed in a stainless steel screen basket, and the basket is attached to the bottom of an agitator under the impeller in a 300 ml Parr pressure reactor. Phenol (116 g) is added to the reactor, and the reactor is purged with nitrogen by multiple pressurizations and ventings, finally being sealed at ambient pressure. The reactor is heated to the desired temperature with stirring. Samples are periodically taken by cooling to about 60°-80° C., venting, removing a fitting on the reactor head and withdrawing a small sample by syringe. Samples are analyzed by the gas chromatographic method described hereinbefore with the results shown in Table II.

TABLE II

| Ex. | Temp. (°C.) | PhOH/ Catalyst Ratio (g/g) | Run Time (hr) | PhOH Conv. (%)[1] | DPO Sel. (%)[2] | DPO as % of Observed Products[3] |
|---|---|---|---|---|---|---|
| 8 | 330 | 11.60 | 3.50 | 16.6 | 85.8 | 87.5 |
| | 330 | 11.60 | 7.50 | 26.6 | 88.6 | 89.5 |
| | 330 | 11.60 | 11.17 | 34.6 | 83.4 | 89.3 |
| | 330 | 11.60 | 15.25 | 38.7 | 87.5 | 89.3 |
| | 330 | 11.60 | 21.25 | 43.9 | 88.6 | 89.4 |
| | 330 | 11.60 | 27.25 | 47.9 | 88.1 | 89.1 |
| | 330 | 11.60 | 42.25 | 53.9 | 88.1 | 88.8 |
| 9 | 330 | 5.47 | 4.00 | 35.5 | 85.9 | 84.9 |
| | 330 | 5.47 | 21.00 | 56.5 | 80.3 | 81.2 |
| | 330 | 5.47 | 25.00 | 57.8 | 81.2 | 82.8 |
| | 330 | 5.47 | 44.00 | 60.0 | 78.2 | 78.8 |
| 10 | 300 | 11.55 | 3.00 | 5.8 | 70.7 | 93.1 |
| | 300 | 11.55 | 20.00 | 14.7 | 82.2 | 93.1 |
| | 300 | 11.55 | 24.00 | 15.9 | 83.4 | 92.2 |
| | 300 | 11.55 | 46.00 | 20.8 | 87.5 | 92.7 |
| | 300 | 11.55 | 51.00 | 21.8 | 84.8 | 92.4 |
| | 300 | 11.55 | 66.00 | 21.8 | 85.8 | 92.7 |
| | 300 | 11.55 | 88.00 | 24.4 | 84.7 | 92.5 |

[1] Phenol (PhOH) conversion is calculated as 100 percent minus the GLC weight percent phenol.
[2] Selectivity to diphenyl oxide (DPO) is calculated as (100)[wt. % DPO/170.2]/[(100- wt. % phenol)/94.1(2)], based on GLC analysis.
[3] Calculated as 100(wt. % DPO)/(wt. % observed products excluding phenol and solvent), based on GLC analysis.

It is seen that dealuminated acid mordenite zeolite catalyzes the liquid phase dehydration of phenol to diphenyl oxide. At a run time of 21.25 hr the catalyst achieves a phenol conversion of 43.9 percent and a selectivity to diphenyl oxide of 88.6 mole percent. At a run time of 42.25 hr the catalyst achieves a phenol conversion of 53.9 percent and a selectivity to diphenyl oxide of 88.1 mole percent.

EXAMPLE 9

The dehydration of phenol is conducted in the liquid phase in a manner similar to Example 8, with the exception that the catalyst comprises a mixture of fresh dealuminated mordenite (10.5208 g), having a silica to alumina molar ratio of 113 pretreated under nitrogen at 400° C. for 2 hr, and regenerated mordenite catalyst (10.6727 g), having a silica to alumina molar ratio of 113. The regenerated mordenite catalyst is prepared by heating a spent mordenite catalyst, taken from a reaction similar to Example 8, under air at 550° C. for 2-3 hr and then cooling under nitrogen to room temperature. Reaction conditions and results are given in Table II. It is seen that a mixture of fresh and regenerated mordenite zeolite catalyzes the liquid phase dehydration of phenol to diphenyl oxide. At a run time of 21.00 hr the catalyst achieves a phenol conversion of 56.5 percent and a selectivity to diphenyl oxide of 80.3 percent. At a run time of 44.00 hr the catalyst achieves a phenol conversion of 60.0 percent and a selectivity to diphenyl oxide of 78.2 percent.

EXAMPLE 10

The dehydration of phenol is conducted in the liquid phase in a manner similar to Example 8, with the exception that the catalyst employed is a regenerated dealuminated mordenite having a silica to alumina molar ratio of 113 and the process temperature is 300° C. rather than 330° C. The regenerated mordenite catalyst is prepared by heating a spent mordenite catalyst, taken from a reaction similar to Example 8, under air at 550° C. for 2-3 hr and then cooling under nitrogen to room temperature. Reaction conditions and results are given in Table II. It is seen that at a run time of 20.00 hr the catalyst achieves a phenol conversion of 14.7 percent and a diphenyl oxide selectivity of 82.2 mole percent. At a run time of 46.00 hr the catalyst achieves a conversion of 20.8 percent and a selectivity to diphenyl oxide of 87.5 mole percent. When Example 10 is compared with Examples 8 and 9, it is observed that the regenerated catalyst of Example 10 exhibits a high selectivity for diphenyl oxide similar to the fresh catalyst, but at the lower process temperature of Example 10 the rate of phenol conversion is slower.

What is claimed is:

1. A process of preparing a diaryl ether comprising contacting a hydroxy-substituted aromatic compound with a catalytic amount of a zeolite selected from the group consisting of dealuminated acidic mordenite, zeolite β and dealuminated zeolite L, the mordenite zeolite being characterized as having a silica to alumina molar ratio of at least about 40 and the β and L zeolites being characterized as having a silica to alumina molar ratio of at least about 20, the contacting occurring under reaction conditions such that a diaryl ether is formed.

2. The process of claim 1 wherein the hydroxy-substituted aromatic compound is phenol or an α- or β-hydroxy-substituted fused aromatic ring system, or substituted derivatives thereof.

3. The process of claim 2 wherein the hydroxy-substituted aromatic compound is phenol.

4. The process of claim 1 wherein a gaseous or liquid diluent is employed with the hydroxy-substituted aromatic compound.

5. The process of claim 1 wherein the zeolite is acidic mordenite.

6. The process of claim 5 wherein the mordenite zeolite has a silica to alumina molar ratio in the range from about 50 to about 500.

7. The process of claim 5 wherein the mordenite is prepared from a starting mordenite having a Symmetry Index in the range from about 0.5 to about 1.3.

8. The process of claim 1 wherein the reaction conditions comprise a temperature in the range from about 200° C. to about 550° C.

9. The process of claim 1 wherein the hydroxy-substituted aromatic compound is in a liquid phase and the reaction conditions comprise a pressure ranging from sub-atmospheric to about 1500 psig.

10. The process of claim 1 wherein the hydroxy-substituted aromatic compound is in a vapor phase and the reaction conditions comprise a pressure ranging from sub-atmospheric to about 200 psig.

11. The process of claim 1 wherein the reaction conditions comprise a weight hourly space velocity ranging from about 0.01 hr$^{-1}$ to about 10 hr$^{-1}$.

12. The process of claim 1 wherein the diaryl ether is diphenyl ether.

13. The process of claim 1 wherein the hydroxy-substituted aromatic compound is reacted in a conversion of at least about 10 weight percent and with a selectivity to diaryl ether of at least about 40 mole percent.

14. The process of claim 1 wherein the hydroxy-substituted aromatic compound is reacted in a conversion of at least about 20 weight percent and with a selectivity to diaryl ether of at least about 60 mole percent.

15. The process of claim 1 wherein the catalyst is regenerated by burn-off in air or oxygen, and optionally in the presence of an inert gaseous diluent, at a temperature in the range from about 300° C. to about 700° C.

16. The process of claim 1 wherein the weight percentage of diaryl ether in the observed products, excluding hydroxy-substituted aromatic compound and solvent, is at least about 70 weight percent.

17. A process of preparing diphenyl oxide comprising contacting liquid phenol with a dealuminated acidic mordenite zeolite having a silica to alumina molar ratio of at least about 40 at a temperature in the range from about 200° C. to about 450° C. and at a pressure in the range from sub-atmospheric to about 1500 psig such that the phenol conversion is at least about 20 weight percent and diphenyl oxide is formed in a selectivity of at least about 80 mole percent.

18. A process of preparing a diaryl ether comprising contacting a hydroxy-substituted aromatic compound with a catalytic amount of a dealuminated zeolite Y having a silica to alumina molar ratio greater than 20, the contacting occurring at a temperature in the range from about 200° C. to about 300° C. and under reaction conditions such that diaryl ether is formed in a selectivity of greater than about 70 weight percent, measured as the weight percentage of diaryl ether found in the observed products excluding hydroxy-substituted aromatic compound and any optional solvent.

19. The process of claim 18 wherein the hydroxy-substituted aromatic compound is selected from the group consisting of phenol, α- and β-hydroxy-substituted fused aromatic ring compounds, and substituted derivatives thereof.

20. The process of claim 18 wherein the hydroxy-substituted aromatic compound is phenol.

21. The process of claim 18 wherein a diluent or solvent is employed with the hydroxy-substituted aromatic compound.

22. The process of claim 18 wherein the reaction conditions comprise a temperature in the range from about 225° C. to about 275° C.

23. The process of claim 18 wherein the hydroxy-substituted aromatic compound is in a liquid phase and the reaction conditions comprise a pressure ranging from sub-atmospheric to about 1500 psig.

24. The process of claim 18 wherein the hydroxy-substituted aromatic compound is in a gaseous phase and the reaction conditions comprise a pressure ranging from sub-atmospheric to about 200 psig.

25. The process of claim 18 wherein the reaction conditions comprise a weight hourly space velocity ranging from 0.01 $hr^{-1}$ to about 10 $hr^{-1}$.

26. The process of claim 18 wherein the diaryl ether is diphenyl ether.

27. The process of claim 18 wherein the weight percentage of diaryl ether in the observed products is at least about 80 weight percent.

* * * * *